(12) United States Patent
Ren et al.

(10) Patent No.: US 6,203,508 B1
(45) Date of Patent: Mar. 20, 2001

(54) THERMAL AND STRESS MAPPING OF BODY LUMENS

(75) Inventors: Brooke Q. Ren, Champlin; Roger N. Hastings, Maple Grove, both of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 08/951,769

(22) Filed: Oct. 16, 1997

(51) Int. Cl.$^7$ ..................................................... A61B 5/03
(52) U.S. Cl. ............................................................. 600/587
(58) Field of Search .................................. 600/549, 587; 604/96–101

(56) References Cited

U.S. PATENT DOCUMENTS

| | | | |
|---|---|---|---|
| 3,533,399 | * 10/1970 | Goldberg et al. | 600/549 |
| 3,661,148 | * 5/1972 | Kolin | 600/587 |
| 3,847,139 | * 11/1974 | Flam | 600/549 |
| 4,046,139 | * 9/1977 | Horn | 600/549 |
| 5,010,892 | * 4/1991 | Colvin et al. | 600/587 |
| 5,316,016 | * 5/1994 | Adams et al. | 600/587 |
| 5,752,522 | * 5/1998 | Murphy | 600/587 |

* cited by examiner

*Primary Examiner*—Max Hindenburg
(74) *Attorney, Agent, or Firm*—Vidas, Arrett & Steinkraus, P.A.

(57) ABSTRACT

The inventive method requires advancing a three-dimensional imaging balloon catheter to the site of a lesion to be imaged, inflating or molding the balloon to image the lesion, deflating the balloon, withdrawing the catheter from the body lumen and re-inflating the balloon which reassumes its memorized shape. Stress and thermal mapping of the balloon is then done by direct observation or by numerical analysis of the material strain and color of the re-inflated 3D imaging balloon.

17 Claims, 2 Drawing Sheets

(1 of 2 Drawing Sheet(s) Filed in Color)

THERMAL AND STRESS MAPPING OF BODY LUMENS

BACKGROUND OF THE INVENTION

The present invention relates to thermal and stress mapping of a body lumen, and more particularly to analyzing the material strain and color of the surface of a lesion molding balloon to classify the type of lesion and whether it is vulnerable to rupture.

It is widely recognized that plaques or lesions can be classified into three broad categories: calcified or hard plaque lesions, fibrous or soft lesions and inflamed soft lipid filled plaques or lesions. The diagnosis of the type of lesion drives the particular treatment of the lesion, whether it is removal of the lesion by rotablator, predilatation by balloon angioplasty, delivery of a stent, with or without predilatation, or the like.

In particular, the identification of inflamed plaques or lesions is important since these lesions are at greatest risk of rupture, which can lead to a large thrombus or blood clot, which can completely occlude the flow of blood through the artery, leading to injury of the heart or brain. An inflamed or vulnerable lesion is characterized by its cap thickness, lipid pool size and inflammation or temperature. This is discussed in great detail in WO 97/10748 published Mar. 27, 1997 and entitled "Detecting Thermal Discrepancies In Vessel Walls", the entire contents of which are hereby incorporated by reference. As discussed in the published PCT application, considerable evidence indicates that plaque rupture triggers 60–70% of fatal myocardial infarctions. As is well known in the art, and described in the published PCT application, an inflamed plaque is hotter than the surrounding tissue. This published PCT patent application relates to using an infrared fiberoptic system to locate inflamed heat producing plaque. However, the device described in this PCT published application is very expensive, making it available in a limited number of procedures. What is needed is a more inexpensive method for classifying plaques or lesions, and in particular determining which plaques are hard, soft or inflamed, which drives the treatment after diagnosis.

SUMMARY OF THE INVENTION

Applicants have discovered that in addition to providing a three-dimensional (3D) image of the geometry of a lesion or plaque in a body lumen, the balloon can be further analyzed to determine its material stress, which can in turn be used to determine the temperature of a lesion as well as the hardness of a plaque or lesion. Differences between the observed material stress and a baseline material stress can also determine temperature differences along the balloon surface, which can be used to aid in determining whether a particular lesion is inflamed and vulnerable to rupture. The material stress of the balloon material manifests itself in the color pattern observed under white light with a polariscope.

The inventive method requires advancing a three-dimensional imaging balloon catheter to the site of a lesion to be imaged, inflating or molding the balloon to image the lesion, deflating the balloon, withdrawing the catheter from the body lumen and re-inflating the balloon which reassumes its memorized shape. Stress mapping of the balloon is then done by analyzing the material strain and color of the re-inflated 3D imaging balloon.

Direct observation of the color pattern which is predominantly blue/green is considered indicative of an inflamed lesion. More precise temperature mapping may be performed by digitizing the surface geometry of the balloon and computing the color pattern based on the digitized surface geometry and the observed narrowest balloon diameter $ID_i$. By comparing the differences between a computed color pattern, which is based on the digitized surface geometry of the balloon, to the observed color pattern, a temperature map can be generated which can be used to determine whether a lesion is an inflamed vulnerable lesion which is at greatest risk of rupture. The color pattern may also be used to determine whether the lesion is a hard calcified lesion.

The comparison of color patterns may be done with a flip-chart of baseline images or by using a computer to match the actual color pattern to a baseline image.

In addition to using a polariscope and analyzing the color patterns, an alternate embodiment of the inventive step would utilize a temperature sensitive balloon material which would change color depending on the temperature of the body lumen, which could vary along its axial length. Using such a temperature sensitive balloon material would allow direct observation of the withdrawn balloon which would provide a temperature map of the body lumen including a lesion, which would then indicate directly whether the lesion was inflamed by observing whether the temperature was higher than the normal body temperature.

BRIEF DESCRIPTION OF THE FIGURE

The file of this patent contains at least one drawing executed in color. Copies of this patent with color drawing(s) will be provided by the Patent amd Trademark office upon request and payment of the necessary fee.

DESCRIPTION OF THE PREFERRED EMBODIMENTS

Figure 1:
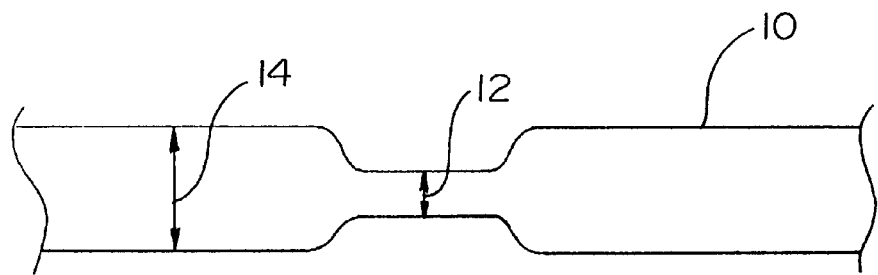
FIG. 1 shows a three-dimensional imaging balloon which has been molded to memorize the geometry of a portion of a body lumen containing a lesion or plaque.

FIG. 1 shows a three-dimensional imaging balloon 10 which has been inflated in a body lumen, memorized the geometry of the body lumen around a lesion, been withdrawn from the body and reinflated to reassume its memorized shape. Co-pending application Ser. No. 08/857791 filed May 16, 1997 describes the three-dimensional imaging balloon 10 (lesion molding balloon) of the preferred embodiment, and its entire contents are hereby incorporated by reference.

The balloon 10 is preferably constructed of semi-crystalline or amorphous blend materials, and more preferably of a blend of PBT and PETG, with a ratio of PBT to PETG ranging from 1:1 to 1:19, by weight. In the preferred embodiment the ratio is 1:3 or 25% PBT and 75% PETG, by weight. The preferred balloon material will deform or yield at approximately 1 atmosphere. The preferred balloon is preferably used in connection with lesions which produce an $ID_i$ of between 2.5 mm and 4.0 mm, as discussed further below.

In use the catheter carrying balloon 10 is tracked to the site of a lesion, expanded to image the geometry of the body lumen, deflated and withdrawn from the body. Typically the balloon 10 will be inflated for 1 minute at 1.5 atm. Upon re-inflating outside the body the balloon 10 will reassume its memorized shape, providing a three-dimensional image of the geometry of the body lumen and lesion.

The reinflated balloon may be measured directly to determine the narrowest diameter of the balloon $ID_i$ and the maximum diameter of the balloon $ID_o$, shown respectfully at 12 and 14 in FIG. 1. The preferred embodiment has been formulated to work best where the $ID_i$ is in the range of 2.5 mm–4 mm.

The balloon material used to construct the three-dimensional imaging balloon (3-D balloon) are anisotropic, and exhibit optical birefringence, which means that light entering the material travels at different speeds along the material principal axes. In the case of the balloon 10, the two axes are the longitudinal and circumferential axes. The relative retardation of light along the two principal axes is proportional to the difference in internal stress loadings along the two axes, which is know as the stress-optic law. For a discussion of the theory of birefringence please see *Experimental Stress Analysis, 2nd Edition,* James W. Dally and William F. Riley, McGraw-Hill, New York, 1978.

Figure 2:
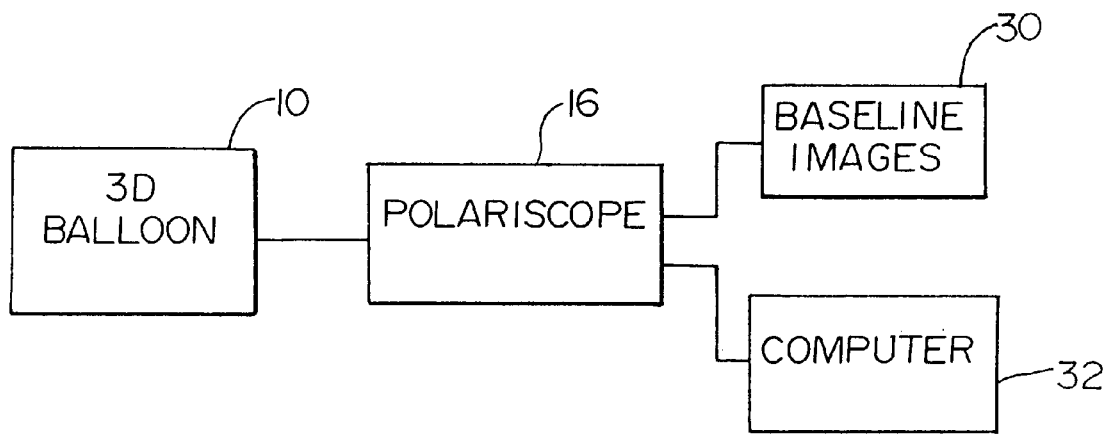
FIG. 2 is a block diagram showing the components used in the method.

The reinflated balloon is viewed through polariscope 16, as shown in FIG. 2. In a polariscope, light is first linearly polarized by passing it through a filter, the filtered light then traverses the balloon material and is finally viewed through a polarizing filter which is placed at right angles to the incident filter. Birefringent materials rotate the plane of polarization, so that some portion of light exits the polariscope. If no material or non-birefringent material were present no light would pass through the polariscope. Monochromatic light passing through the polariscope appears as patterns of dark and light caused by the optical interference of the two principal axes light waves. Viewed in white light, the patterns appear as colored bands or regions on the balloon material (best seen in FIG. 3). The color pattern changes as the material object is rotated within the polariscope, therefore to enable proper comparison a fixed viewing angle or orientation must be used in viewing balloon 10 under the polariscope. Given a fixed viewing angle or orientation the color observed at a given point on the balloon material will be determined by the relative retardation, or the relative stress between the optical axes, the longitudinal and circumferential axes of the balloon 10.

Balloon 10 is prestretched longitudinally which uniaxially orients the balloon material, inducing internal stress along the longitudinal axis. When the balloon 10 is inflated or "molded" in the body lumen the longitudinal stress is relieved and circumferential or hoop stress increases with increasing balloon diameter. Therefore, the molded balloon 10 shows a color which depends upon its diameter, and when the balloon is molded with a lesioned vessel of variable geometry and diameter, a pattern of colors appears in the polariscope. When the balloon is molded in a body lumen which has been heated by even a few degrees C (caused for example by an inflamed lesion), the elevated temperature reduces stresses built up in the balloon material, and the color pattern changes to shorter wavelengths indicating less retardation. If the lesion is heated in localized spots, these spots will show shorter wavelengths than the surrounding areas.

Figure 3:
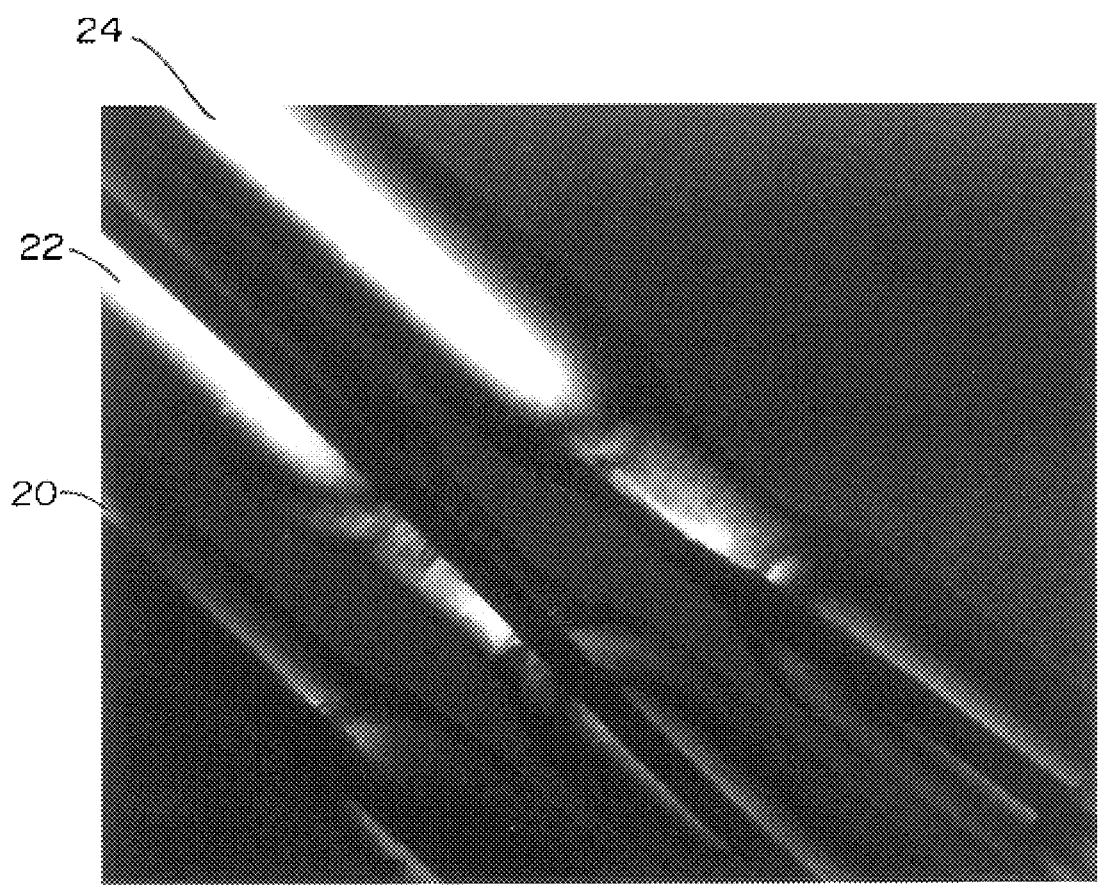
FIG. 3 is a color photo showing the color pattern produced by the polariscope of calcified, soft and inflamed lesions or plaques.

FIG. 3 shows three different balloons molded under different conditions. Reference numeral 20 shows the image produced under a polariscope of a hard calcified lesion, 5 mm long, with $ID_i$=2.5 mm, $ID_o$=5 mm and the lesion temperature at 37° C. The balloon shown at 22 shows the image produced under a polariscope of a soft fibrous lesion, 5 mm long, with $ID_i$=2.75 mm, $ID_o$=5 mm and the lesion temperature at 37° C. The balloon shown at 24 shows the image produced under a polariscope of the same soft material, but with a lesion temperature at 40° C. to simulate an inflamed lipid filled vulnerable lesion, 5 mm long with $ID_i$=2.75 mm, $ID_o$=5 mm.

Applicants have observed that inflamed lesions shift the color patterns to a blue/green pattern as shown at 24, which is quite distinctive and different than the color patterns shown at 20 and 22. It is believed that over a range of diameters, the blue/green color pattern such as shown at 24 will only be caused by an inflamed lesion, which is hotter and shifts the wavelengths to the blue/green color pattern observed at 24.

Therefore, direct observation of the balloon material under the polariscope can allow diagnosis of whether the lesion is inflamed by directly observing the color pattern and visually determining the temperature map of the balloon surface.

An alternate embodiment of the inventive method would utilize a temperature sensitive balloon material, or coating or film covering the balloon material, which would directly change color depending on the temperature of the body lumen coming into contact with the balloon material. This would allow a direct observation of the temperature map of the body lumen and lesion by simply viewing the balloon material after withdrawal from the body, eliminating the need for a polariscope or the more elaborate computation steps discussed below.

As can be seen the balloon at 20 has a predominately solid purple color indicating a lesion whose diameter is axially the same along the lesion length. Testing has indicated that there may be some correlation between color and lesion hardness, with the shorter wavelengths of purple indicating a hard lesion and the longer wavelengths of yellow and orange indicating a softer lesion. This may be due to the greater material stress caused by expanding the balloon against a hard lesion versus a soft lesion, which affects the relative stress between the optical axes of the balloon material.

In a preferred embodiment, the balloon material is viewed under the polariscope and a determination made as to whether the lesion is inflamed by observing the blue/green color pattern. It is believed that the temperature affects to the color pattern outweigh the diameter effects to the color pattern, since blue/green has only been observed in connection with inflamed lesions, even across a larger range of diameters.

To more precisely determine a temperature map of the lesion, the geometry of the surface of the reinflated three-dimensional imaging balloon 10 is digitized and input into computer 32. A baseline or computed color pattern may be calculated based solely on the geometry of the balloon material, given the color observed at the narrowest diameter $ID_i$ and assuming that strain is proportional to stress in the balloon material. This computed color pattern only takes into account the diameter changes which affect the color pattern. Any differences between the actual observed color pattern and the computed color pattern are believed due to either hardness of the lesion or temperature of the lesion. Furthermore, it is believed that the temperature effects outweigh the hardness effects. Therefore, the differences in the color pattern can be used to quantify the surface temperature distribution of the balloon material. A temperature map of the lesion could then be generated and used to determine whether the lesion was hotter than the surrounding body lumen, indicative of an inflamed lesion.

In another embodiment, a series of baseline images or photos 30 can be prepared relative to the parameters which affect color pattern. For example a set of photos could be produced at 10 different diameters $ID_i$, hard versus soft, and at 4 different temperatures. Once the $ID_i$ is determined by measuring the reinflated balloon at its narrowest diameter, the user could visually compare the color pattern observed under the polariscope with a flip-chart of images at a particular $ID_i$. A match would identify the hardness and temperature of the lesion. It has been observed that calcified lesions do not exhibit the higher temperatures associated with inflamed lesions. The images or photos could also be loaded into computer 32 and a pattern matching program could automate the matching of the observed color pattern to a baseline color pattern.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A method of mapping a body lumen comprising the steps of:
   providing a catheter with a three-dimensional imaging balloon near a distal end of the catheter;
   advancing the distal end of the catheter to the portion of the body lumen to be mapped;
   expanding the balloon so that the balloon molds itself to and memorizes the three-dimensional geometry of the portion of the body lumen to be mapped;
   deflating the balloon;
   withdrawing the distal end of the catheter from the body lumen;
   reinflating the three-dimensional imaging balloon, which reassumes the memorized three-dimensional geometry of the portion of the body lumen to be mapped;
   stress mapping the portion of the body lumen to be mapped by analyzing the material strain of the reinflated three-dimensional imaging balloon.

2. The method of claim 1 wherein the material strain is analyzed by viewing the reinflated three-dimensional imaging balloon under a polariscope.

3. The method of claim 1 wherein the material strain is analyzed by digitizing the geometry of the surface of the reinflated three-dimensional imaging balloon and calculating the material strain.

4. The method of claim 2 wherein the reinflated three-dimensional imaging balloon is viewed under the polariscope using white light, which due to the optical birefringence of the three-dimensional imaging balloon material creates a color pattern on the balloon where the color at each point is determined by the relative stress between the longitudinal and circumferential axes of the balloon.

5. The method of claim 4 further including the step of:
   classifying a lesion in the portion of the body lumen mapped by determining the distribution of the lesions compressibility along its longitudinal length based on the color pattern viewed under the polariscope.

6. The method of claim 5 further including the step of:
   thermally mapping the lesion by determining the differences between a computed material strain, determined by digitizing the geometry of the surface of the reinflated three-dimensional imaging balloon and calculating the material strain, and the actual material strain, where the differences are used to determine the surface temperature distribution.

7. The method of claim 5 further including the step of:
   thermally mapping the lesion by determining the differences between the color pattern viewed under the polariscope and the color pattern of a set of baseline images.

8. The method of claim 5 further including the step of classifying a lesion as a calcified lesion by determining that the lesion is relatively incompressible along its longitudinal length.

9. The method of claim 5 further including the step of classifying a lesion as a fibrous lesion by determining that the lesion is compressible along its longitudinal length.

10. The method of claim 5 further including the step of classifying a lesion as a vulnerable lipid filled lesion by determining that the lesion is very compressible along its longitudinal length.

11. A method of stress and thermal mapping a body lumen comprising the steps of:
   providing a catheter with a three-dimensional imaging balloon near a distal end of the catheter;
   advancing the distal end of the catheter to a portion of the body lumen containing a lesion;
   expanding the balloon so that the balloon molds itself to and memorizes the three-dimensional geometry of the lesion;
   deflating the balloon;
   withdrawing the distal end of the catheter from the body lumen;
   reinflating the three-dimensional imaging balloon, which reassumes the memorized three-dimensional geometry of the portion of the body lumen containing the lesion;
   digitizing the geometry of the surface of the reinflated three-dimensional imaging balloon;
   viewing the reinflated balloon under a polariscope using white light, which due to the optical birefringence of the three-dimensional imaging balloon material creates a color pattern on the balloon where the color at each point is determined by the relative stress between the longitudinal and circumferential axes of the balloon;
   calculating the material strain of the balloon surface based on the digitized geometry of the balloon surface;
   calculating a baseline color pattern based on the calculated material strain of the balloon surface;
   classifying the type of lesion based on the calculated material strain of the balloon surface, and
   determining whether the lesion is vulnerable by comparing the viewed color pattern to the calculated baseline color pattern, where the differences between the viewed and calculated color patterns quantify the surface temperature distribution of the lesion.

12. A method of thermally mapping a body lumen comprising the steps of:
   providing a catheter with a three-dimensional imaging balloon near a distal end of the catheter;
   advancing the distal end of the catheter to the portion of the body lumen to be mapped;
   expanding the balloon so that the balloon molds itself to and memorizes the three-dimensional geometry of the portion of the body lumen to be mapped;
   deflating the balloon;
   withdrawing the distal end of the catheter from the body lumen;
   reinflating the three-dimensional imaging balloon, which reassumes the memorized three-dimensional geometry of the portion of the body lumen to be mapped;

determining a temperature map of the body lumen by observing the reinflated balloon.

13. The method of claim 12 wherein the balloon material is temperature sensitive and direct observation determines the temperature map of the body lumen.

14. The method of claim 12 further including the step of:

viewing the balloon material with a polariscope under white light, which produces a color pattern on the balloon material, and direct observation of the color pattern determines the temperature map of the body lumen.

15. The method of claim 12 further including the steps of:

viewing the balloon material with a polariscope under white light, which produces a color pattern on the balloon material;

calculating the color pattern based on the digitized geometry and the color observed at the narrowest balloon diameter;

determining a temperature map of the body lumen by comparing the differences between the viewed color pattern and calculated color pattern.

16. A system of stress mapping a portion of a body lumen, comprising:

an elongate catheter having a distal end and having a three-dimensional imaging balloon near a distal end of the catheter for memorizing the three-dimensional geometry of a portion of a body lumen, the elongate catheter being removed from the body lumen and reinflated after memorizing the three-dimensional geometry of a portion of body lumen;

a stress mapping device for analyzing the material strain of the reinflated three-dimensional imaging balloon.

17. The system of claim 16 wherein the stress mapping device is a polariscope.

* * * * *